United States Patent [19]

Fujimura et al.

[11] 4,293,713
[45] Oct. 6, 1981

[54] NOVEL 1,1,3,5-SUBSTITUTED BIURET COMPOUND AND A PHARMACEUTICAL COMPOSITION CONTAINING THE SAME

[75] Inventors: Hajime Fujimura, Kyoto; Yasuzo Hiramatsu, Otsu; Takahiro Yabuuchi, Takarazuka; Masakatu Hisaki, Hikone; Katsuo Takikawa, Naruto; Takaji Honna, Tokushima; Hidekazu Miyake, Tokushima; Makoto Kajitani, Tokushima, all of Japan

[73] Assignee: Taiho Pharmaceutical Company Limited, Tokyo, Japan

[21] Appl. No.: 134,556

[22] Filed: Mar. 27, 1980

[30] Foreign Application Priority Data

Mar. 31, 1979 [JP] Japan .................................. 54-38790

[51] Int. Cl.³ .................... A61K 31/17; C07C 127/24
[52] U.S. Cl. ........................................ 564/38; 424/322
[58] Field of Search .......................................... 564/38

[56] References Cited

U.S. PATENT DOCUMENTS

| | | | |
|---|---|---|---|
| 3,149,338 | 9/1964 | Habicht et al. | 564/38 X |
| 3,189,431 | 6/1965 | Salzberg | 71/2.6 |
| 3,253,902 | 5/1966 | Münz et al. | 564/38 X |
| 3,305,549 | 2/1967 | Chubb | 564/38 X |
| 3,407,193 | 10/1968 | McColl et al. | 564/38 X |
| 3,556,766 | 1/1971 | Mitchell | 564/38 |

FOREIGN PATENT DOCUMENTS

1096006 12/1967 United Kingdom .

OTHER PUBLICATIONS

Kogon, CA 53:7064e (1958).
Hill, J. Amer. Chem. Soc. 62, 1595 (1940).
Thurman et al., J. Heterocyclic Chemistry, 9, 459–460 (1972).

*Primary Examiner*—John Doll
*Attorney, Agent, or Firm*—Murray and Whisenhunt

[57] ABSTRACT

A novel 1,1,3,5-substituted biuret compound of the formula:

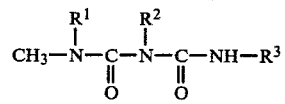

wherein $R^1$ and $R^2$ are respectively the same or different, and each are alkyl groups having 1 to 4 carbon atoms; $R^3$ is a cyclohexyl group or a phenyl group which may be unsubstituted or may have at least one substituent selected from the group consisting of chlorine, bromine, fluorine, methyl, trifluoromethyl, dimethylamino, methoxy, methylthio, nitro and acetyl. The novel 1,1,3,5-substituted biuret compounds are useful as an analgesic, anti-inflammatory and/or antipyretic agent.

33 Claims, No Drawings

NOVEL 1,1,3,5-SUBSTITUTED BIURET COMPOUND AND A PHARMACEUTICAL COMPOSITION CONTAINING THE SAME

The present invention relates to a novel 1,1,3,5-substituted biuret compound and to a pharmaceutical composition containing the same.

Although the definitions of $R^1$, $R^2$ and $R^3$ in the formula (1) are different, some 1,1,3,5-substituted biuret compounds have been known before. [cf. British Pat. No. 1,096,006; U.S. Pat. No. 3,189,431; J. Amer. Chem. Soc., 62, 1595 (1940) and J. Heterocyclic Chem., 9, 459–460 (1972)]. However, most of these known 1,1,3,5-substituted biuret compounds have simply been known as chemical substances but the effectiveness thereof have not been known widely, and only few such compounds have been known as herbicide.

The present invention is based upon the fact that the novel 1,1,3,5-substituted biuret compounds have useful analgesic, anti-inflammatory and/or anti-pyretic activitie(s).

The object of the present invention is to provide novel 1,1,3,5-substituted biuret compounds.

Another object of the present invention is to provide an analgesic, anti-inflammatory and/or anti-pyretic composition containing the same.

Said novel 1,1,3,5-substituted biuret compound is represented by the formula (1):

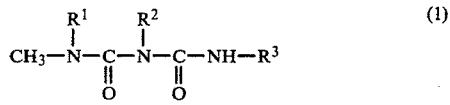

wherein $R^1$ and $R^2$ are respectively the same or different, and each are alkyl groups having 1 to 4 carbon atoms; $R^3$ is a cyclohexyl group or a phenyl group which may be unsubstituted or may have at least one substituent selected from the group consisting of chlorine, bromine, fluorine, methyl, trifluoromethyl, dimethylamino, methoxy, methylthio, nitro and acetyl; and is useful as an analgesic, anti-inflammatory and/or anti-pyretic agent.

Among the novel 1,1,3,5-substituted biuret compounds of the formula (1), the following compounds are preferred:
1,1,3-Trimethyl-5-phenylbiuret
1,1,3-Trimethyl-5-(2-fluorophenyl)biuret
1,1,3-Trimethyl-5-(4-fluorophenyl)biuret
1,1,3-Trimethyl-5-(2,3,5,6-tetrafluorophenyl)-biuret
1,1,3-Trimethyl-5-(2-chlorophenyl)biuret
1,1,3-Trimethyl-5-(3-chlorophenyl)biuret
1,1,3-Trimethyl-5-(4-chlorophenyl)biuret
1,1,3-Trimethyl-5-(2,4-dichlorophenyl)biruet
1,1,3-Trimethyl-5-(2,6-dichlorophenyl)biuret
1,1,3-Trimethyl-5-(3,4-dichlorophenyl)biuret
1,1,3-Trimethyl-5-(4-bromophenyl)biuret
1,1,3-Trimethyl-5-(2-trifluoromethylphenyl)biruet
1,1,3-Trimethyl-5-(3-trifluoromethylphenyl)biuret
1,1,3-Trimethyl-5-(4-dimethylaminophenyl)biuret
1,1,3-Trimethyl-5-(4-nitrophenyl)biuret
1,1,3-Trimethyl-5-(2-methoxyphenyl)biuret
1,1,3-Trimethyl-5-(4-methoxyphenyl)biuret
1,1,3-Trimethyl-5-(3,4-dimethoxyphenyl)biuret
1,1,3-Trimethyl-5-(3,4,5-trimethoxyphenyl)biuret
1,1,3-Trimethyl-5-(2-methylphenyl)biuret
1,1,3-Trimethyl-5-(3-methylphenyl)biuret
1,1,3-Trimethyl-5-(4-methylphenyl)biuret
1,1,3-Trimethyl-5-(2,3-dimethylphenyl)biuret
1,1,3-Trimethyl-5-(2,6-dimethylphenyl)biuret
1,1,3-Trimethyl-5-(3,4-dimethylphenyl)biuret
1,1,3-Trimethyl-5-(2-methyl-3-chlorophenyl)biuret
1,1,3-Trimethyl-5-(4-acetylphenyl)biuret
1,1,3-Trimethyl-5-(4-methylthiophenyl)biuret
1,1,3-Trimethyl-5-cychlohexylbiuret
1,1-Dimethyl-3-ethyl-5-phenylbiuret
1,1-Dimethyl-3-n-propyl-5-phenylbiuret
1,1-Dimethyl-3-n-butyl-5-phenylbiuret
1-Ethyl-1,3-dimethyl-5-phenylbiuret
1-n-Propyl-1,3-dimethyl-5-phenylbiuret
1-n-Butyl-1,3-dimethyl-5-phenylbiuret
one group of preferred compounds of the formula (1) includes compounds wherein each of $R^1$ and $R^2$ are methyl.

Another group of preferred compound of the formula (1) includes compounds wherein $R^3$ is unsubstituted or substituted phenyl.

Another group of preferred compounds of formula (1) includes compounds wherein each of $R^1$ and $R^2$ are methyl and $R^3$ is unsubstituted or substituted phenyl.

The 1,1,3,5-substituted biuret compound of the formula (1) can be prepared by processes as shown below.

Reaction process-A

Reaction of an urea compound of the formula (2) with an isocyanate compound of the formula (3) to obtain the 1,1,3,5-substituted biuret compound of the formula (1) is shown as follows:

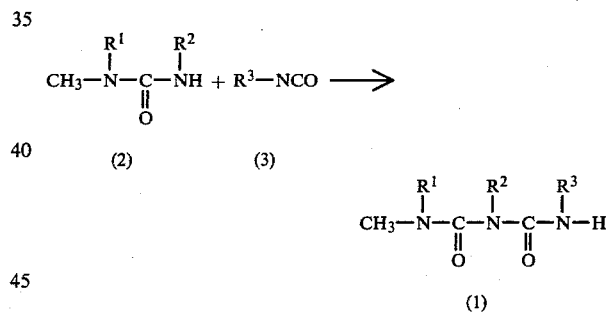

In this reaction process A, the reaction of an urea compound of the formula (2) with an isocyanate compound of the formula (3) may be carried out in a solvent in the presence of a catalyst.

Reaction process A-1

As to the catalyst, basic compounds such as sodium hydride, sodium amide and the like can be used. The solvent used in this reaction is not subjected to any specific restriction and may be of any inert type which gives no adverse effect to the reaction. Among the examples of the solvents are ethers such as ether, dioxane, tetrahydrofuran and the like; aromatic hydrocarbons such as benzene, toluene, xylene and the like. The ratio of amounts of the urea compound (2), the isocyanate compound (3) and the catalyst in this reaction is not subjected to any specific restriction and may be suitably selected from a wide range, and usually, it is desirable that they are used in equimolar quantity respectively. The reaction temperature is also not subjected to any particular restriction and may be suitably selected from a wide range, and usually the reaction can be carried out at −20° C. to a room temperature.

Reaction process A-2

As to the catalyst, Lewis acids such as anhydrous aluminium chloride, anhydrous stannic chloride, titanium tetrachloride or the like can be used. The solvent used in this reaction is not subjected to any specific restriction and any known inert type which gives no adverse effect to the reaction can be used. Among the examples of the solvents are halogenated lower alkanes such as methylene chloride, chloroform, carbon tetrachloride and the like; aromatic hydrocarbons such as benzene, toluene, xylene and the like. The ratio of amounts of the urea compound (2), the isocyanate compound (3) and the catalyst in this reaction is not subjected to any specific restriction and may be suitably selected from a wide range, and usually, it is desirable that they are used in equimolar quantity respectively. The reaction temperature is also not subjected to any particular restriction and may be suitably selected from a wide range, and usually the reaction can be carried out at −20° C. to a room temperature. In this reaction, the 1,1,3,5-substituted biuret compound of the formula (1) is formed as a complex with the Lewis acid, and a free form of the biuret compound of the formula (1) can easily be obtained by treating the complex with a diluted mineral acid such as a diluted hydrochloric acid or a diluted sulfuric acid at a room temperature under stirring condition. The thus obtained free form of the biuret compound of the formula (1) can easily be isolated by usual separation means.

Reaction process B

Reaction of an allophanoyl chloride of the formula (4) with an amine of the formula (5) to obtain the 1,1,3,5-substituted biuret compound of the formula (1) is shown as follows:

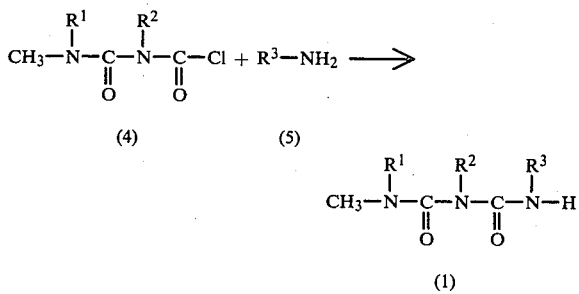

In this reaction process B, the reaction of an allophanoyl chloride of the formula (4) with an amine of the formula (5) may be carried out in a solvent. The solvent used in this reaction is not subjected to any specific restriction and may be of any known inert type which gives no adverse effect to the reaction. Among the examples of the solvents are ethers such as ether, dioxane, tetrahydrofuran and the like; halogenated lower alkanes such as methylene chloride, chloroform, carbon tetrachloride and the like; aromatic hydrocarbons such as benzene, toluene, xylene and the like. If necessary, basic compounds such as triethylamine, pyridine and the like may be used as suitable condensation agent. The ratio of amount of the allophanoyl chloride (4) and the amine (5) in this reaction may be suitably selected from a wide range, and usually, it is desirable that the amine (5) is used in equimolar to 2 times the molar quantity of the allophanoyl chloride (4). The reaction temperature is also not subjected to any particular restriction, and the reaction is usually carried out in the range of from −20° C. to +50° C. In this reaction, the 1,1,3,5-substituted biuret compound of the formula (1) thus formed can easily be isolated by usual separation means.

Alternatively, the 1,1,3,5-substituted biuret compound of the formula (1) can also be prepared by reacting an allophanoyl chloride of the formula (6) with an amine of the formula (7) as follows:

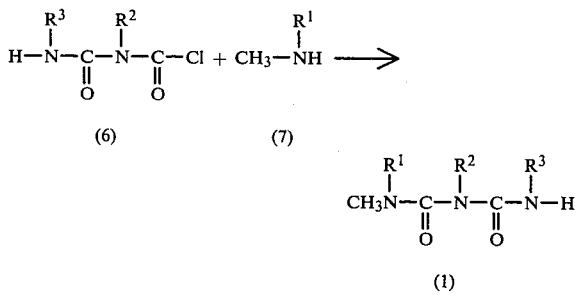

The reaction of the allophanoyl chloride (6) with the amine (7) is carried out under a condition similar to the reaction condition of the allophanoyl chloride (4) with the amine (5) as mentioned above.

The 1,1,3,5-substituted biuret compound of the formula (1) of the present invention can be administered in the range of from 10 to 2,000 mg per day, preferably from 50 to 1,000 mg per day, for an adult, as an analgesic, anti-inflammatory or anti-pyretic agent. The administration of the compound is generally carried out by dividing the above-mentioned daily dosage into 2 or 3 portions. Said dosage of the compound may be adjusted in consideration of the clinical conditions and age of the patient, and may conveniently be administered orally or topically or by injection or suppository.

An analgesic, anti-inflammatory or anti-pyretic agent containing the present biuret compound of the formula (1) is prepared and administered by formulating the present biuret compound with conventional pharmaceutically acceptable carriers or excipients through a common method.

Peroral preparations such as tablets, capsules, granules, powders, etc. may contain excipients used generally in the art. Said excipients are exemplified such as calcium carbonate, calcium phosphates, starch, sucrose, lactose, talc, magnesium stearate, gelatine, polyvinylpyrrolidone, gum arabic, sorbitol, microcrystalline cellulose, polyethyleneglycol, carboxymethylcellulose, silica, polyvinylacetal diethylaminoacetate, hydroxypropyl methylcellulose, shellac, etc. Further, the tablets may be coated with a suitable coating by a common method known in the arts. Peroal liquid form preparations may be of aqueous or oily suspensions, syrups, elixiers and the like and are prepared by common methods. Injection preparations may be of aqueous or oily suspensions, powdery or lyophilyzed preparations which are dissolved upon use. These preparations may be prepared by a common method.

The present substituted biuret compound may also be administered as a suppository composition for rectal use, which may be contain pharmaceutically acceptable carriers, known in the art, such as polyethylene glycols, lanoline, cacao butter, fatty acid triglycerides, etc.

As to preparations for external use, the substituted biuret compound of the present invention may be administered in the form of an ointment or cream which is prepared by formulating the biuret compound with a suitable ointment base and other additives by common method.

EXAMPLES OF THE INVENTION

The present invention is further explained in detail by illustrating examples of synthesis of the substituted biuret compounds in Table 1; and pharmacological tests including analgesic activity test, anti-inflammatory activity test and anti-pyretic activity test in Table 2 together with examples of pharmaceutical preparations.

EXAMPLE 1

Synthesis of 1,1,3-trimethyl-5-p-chlorophenylbiuret (Compound No. 7 in Table 1) by reaction process A-1

Into 200 ml of anhydrous tetrahydrofuran, 2.9 g (0.06 mol) of sodium hydride (50% in oil) was added. The mixture was cooled below 10° C., and 6.1 g (0.06 mol) of 1,1,3-trimethylurea was added thereinto under stirring. The reaction mixture was further stirred at a room temperature for 15 hours and then was cooled below 0° C. Next a solution obtained by dissolving 9.2 g (0.06 mol) of p-chlorophenyl isocyanate in 50 ml of anhydrous tetrahydrofuran was added drop-wise into the reaction mixture under stirring. After the reaction was continued at about 0° C. for 3 hours, the solvent was removed by distillation under a reduced pressure to obtain a residue, and ice-water was added thereinto. The obtained mixture was made acidic by adding a suitable amount of 1 N-hydrochloric acid and then was extracted with chloroform. The chloroform layer was separated and was dried with anhydrous sodium sulfate. The chloroform was removed by distillation under a reduced pressure and the residue thus obtained was recrystallized from ethanol to obtain 10.7 g (yield: 70%) of 1,1,3-trimethyl-5-p-chlorophenylbiuret having a melting point of 94.5°–95° C.

EXAMPLE 2

Synthesis of 1,3-dimethyl-1-propyl-5-phenylbiuret (Compound No. 34 in Table 1) by reaction process A-2

Into 300 ml of anhydrous dichloromethane, 13.0 g (0.1 mol) of 1,3-dimethyl-1-propylurea and 12.0 g (0.1 mol) of phenylisocyanate were added and dissolved. The mixture was ice-cooled under stirring and 26.0 g (0.1 mol) of stannic chloride was added drop-wise. The reaction was then continued at a room temperature for 15 hours and the precipitate formed was separated by filtration. The precipitate thus obtained was added into a mixture of 60 ml of 20% hydrochloric acid/120 ml of chloroform and the stirring was continued until the mixture became transparent. Then the chloroform layer was separated and was washed with water and the chloroform layer was dried with anhydrous sodium sulfate. The chloroform was removed by distillation under reduced pressure and the residue thus obtained was recrystallized from ligroin to obtain 18.6 g (yield: 75%) of 1,3-dimethyl-1-propyl-5-phenylbiuret having a melting point of 63° to 64° C.

EXAMPLE 3

Synthesis of 1,1,3-trimethyl-5-phenylbiuret (Compound No. 1 in Table 1) by reaction process-B Into 50 ml of anhydrous tetrahydrofuran, 7.4 g (0.08 mol) of aniline was added thereinto and dissolved and the mixture was cooled below 0° C. under stirring. Into this cooled mixture, a solution obtained by dissolving 6.4 g (0.04 mol) of 2,4,4-trimethylallophanoyl chloride in 10 ml of anhydrous tetrahydrofuran was added drop-wise under stirring. After the reaction was continued for 1 hour at room temperature, the solvent was removed by distillation under reduced pressure. To the residue thus obtained, water was added and insoluble material was separated by filtration and was recrystallized from ethanol to obtain 13.0 g (yield: 73%) of 1,1,3-trimethyl-5-phenylbiuret having a melting point of 89.5°–90.5° C.

In the following Table 1, there are mentioned the physico-chemical properties of novel 1,1,3,5-substituted biuret compounds, including the compounds prepared in Examples 1–3.

TABLE 1

$$CH_3-\underset{\underset{R^1}{|}}{N}-\underset{\underset{O}{\|}}{C}-\underset{\underset{R^2}{|}}{N}-\underset{\underset{O}{\|}}{C}-\underset{\underset{R^3}{|}}{N}H$$

| Compound No. | $R^1$ | $R^2$ | $R^3$ | Reaction process | MP (°C.) | UV$\lambda_{max}^{cyclohexane}$ m$\mu$ ($\epsilon$) | Molecular formula | Elemental analysis (%) Calculated: (Found:) C | H | N |
|---|---|---|---|---|---|---|---|---|---|---|
| 1 | —CH$_3$ | —CH$_3$ |  | B | 89.5–90.5 | 245(17800) | C$_{11}$H$_{15}$N$_3$O$_2$ | 59.71 (59.79) | 6.83 (6.92) | 18.99 (18.75) |
| 2 | —CH$_3$ | —CH$_3$ |  | B | 66.5–68 | 241.5(19200) | C$_{11}$H$_{14}$FN$_3$O$_2$ | 55.22 (55.28) | 5.90 (5.91) | 17.56 (17.42) |
| 3 | —CH$_3$ | —CH$_3$ |  | B | 73.5–74.5 | 241.5(15800) | C$_{11}$H$_{14}$FN$_3$O$_2$ | 55.22 (55.17) | 5.90 (6.04) | 17.56 (17.39) |
| 4 | —CH$_3$ | —CH$_3$ | 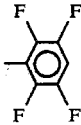 | B | 103.5–105 | 232(15600) | C$_{11}$H$_{11}$F$_4$N$_3$O$_2$ | 45.06 (44.87) | 3.78 (3.84) | 14.33 (14.11) |

TABLE 1-continued $$\underset{CH_3}{\overset{R^1}{\phantom{|}}}N-\underset{\underset{O}{\|}}{C}-\underset{R^2}{\overset{}{\phantom{|}}}N-\underset{\underset{O}{\|}}{C}-\underset{R^3}{\overset{}{\phantom{|}}}NH$$

| Compound No. | $R^1$ | $R^2$ | $R^3$ | Reaction process | MP, (°C.) | UV$\lambda_{max}^{cyclohexane}$ m$\mu$ ($\epsilon$) | Molecular formula | Elemental analysis (%) Calculated: (Found:) C | H | N |
|---|---|---|---|---|---|---|---|---|---|---|
| 5 | —CH$_3$ | —CH$_3$ | 2-Cl-C$_6$H$_4$ | A-1 | 89.5–91 | 247(16400) | C$_{11}$H$_{14}$ClN$_3$O$_2$ | 51.70 (51.59) | 5.52 (5.59) | 16.43 (16.39) |
| 6 | —CH$_3$ | —CH$_3$ | 3-Cl-C$_6$H$_4$ | A-1 | 87–89 | 247(19000) | C$_{11}$H$_{14}$ClN$_3$O$_2$ | 51.70 (51.46) | 5.52 (5.51) | 16.43 (16.23) |
| 7 | —CH$_3$ | —CH$_3$ | 4-Cl-C$_6$H$_4$ | A-1 | 94.5–95 | 250(22700) | C$_{11}$H$_{14}$ClN$_3$O$_2$ | 51.70 (51.63) | 5.52 (5.56) | 16.43 (16.55) |
| 8 | —CH$_3$ | —CH$_3$ | 2,3-Cl$_2$-C$_6$H$_3$ | B | 69.5–70 | 253(23400) | C$_{11}$H$_{13}$Cl$_2$N$_3$O$_2$ | 45.54 (45.46) | 4.52 (4.57) | 14.48 (14.47) |
| 9 | —CH$_3$ | —CH$_3$ | 2,5-Cl$_2$-C$_6$H$_3$ | B | 140–141 | 235(sh) | C$_{11}$H$_{13}$Cl$_2$N$_3$O$_2$ | 45.54 (45.58) | 4.52 (4.36) | 14.48 (14.56) |
| 10 | —CH$_3$ | —CH$_3$ | 3,4-Cl$_2$-C$_6$H$_3$ | B | 123–124 | 253(23900) | C$_{11}$H$_{13}$Cl$_2$N$_3$O$_2$ | 45.54 (45.33) | 4.52 (4.52) | 14.48 (14.48) |
| 11 | —CH$_3$ | —CH$_3$ | 4-Br-C$_6$H$_4$ | B | 105–106 | 252(24500) | C$_{11}$H$_{14}$BrN$_3$O$_2$ | 44.02 (43.67) | 4.70 (4.73) | 14.00 (13.91) |
| 12 | —CH$_3$ | —CH$_3$ | 2-CF$_3$-C$_6$H$_4$ | B | 72–73 | 244(16700) | C$_{12}$H$_{14}$F$_3$N$_3$O$_2$ | 49.83 (49.84) | 4.88 (4.89) | 14.53 (14.14) |
| 13 | —CH$_3$ | —CH$_3$ | 3-CF$_3$-C$_6$H$_4$ | B | 69–69.5 | 245(21100) | C$_{12}$H$_{14}$F$_3$N$_3$O$_2$ | 49.83 (49.83) | 4.88 (4.64) | 14.53 (14.46) |
| 14 | —CH$_3$ | —CH$_3$ | 4-N(CH$_3$)$_2$-C$_6$H$_4$ | B | 124–126 | 273(20600) | C$_{13}$H$_{20}$N$_4$O$_2$ | 59.07 (59.32) | 7.63 (7.56) | 21.20 (21.08) |
| 15 | —CH$_3$ | —CH$_3$ | 4-NO$_2$-C$_6$H$_4$ | B | 157–159 | 310(15400) | C$_{11}$H$_{14}$N$_4$O$_2$ | 49.62 (49.63) | 5.30 (5.33) | 21.04 (21.06) |
| 16 | —CH$_3$ | —CH$_3$ | 2-CH$_3$O-C$_6$H$_4$ | B | 112–113.5 | 247(16000) | C$_{12}$H$_{17}$N$_3$O$_3$ | 57.36 (57.57) | 6.82 (6.86) | 16.72 (16.58) |
| 17 | —CH$_3$ | —CH$_3$ | 4-OCH$_3$-C$_6$H$_4$ | B | 87.5–89 | 250.5(17500) | C$_{12}$H$_{17}$N$_3$O$_3$ | 57.36 (57.49) | 6.82 (6.83) | 16.72 (16.50) |
| 18 | —CH$_3$ | —CH$_3$ | 3,4-(OCH$_3$)$_2$-C$_6$H$_3$ | B | 96.5–98.5 | 253.5(13100) | C$_{13}$H$_{19}$N$_3$O$_4$ | 55.50 (55.22) | 6.81 (6.94) | 14.94 (14.72) |
| 19 | —CH$_3$ | —CH$_3$ | 3,4,5-(OCH$_3$)$_3$-C$_6$H$_2$ | B | 133–135 | 256(14300) | C$_{14}$H$_{21}$N$_3$O$_5$ | 54.01 (54.00) | 6.80 (7.09) | 13.50 (13.54) |
| 20 | —CH$_3$ | —CH$_3$ | 2-CH$_3$-C$_6$H$_4$ | B | 59.5–60 | 246(15200) | C$_{12}$H$_{17}$N$_3$O$_2$ | 61.26 (61.28) | 7.28 (7.48) | 17.86 (17.76) |
| 21 | —CH$_3$ | —CH$_3$ | 3-CH$_3$-C$_6$H$_4$ | B | 98–99 | 246(17100) | C$_{12}$H$_{17}$N$_3$O$_2$ | 61.26 (61.39) | 7.28 (7.43) | 17.86 (17.76) |
| 22 | —CH$_3$ | —CH$_3$ | 4-CH$_3$-C$_6$H$_4$ | B | 115–117 | 247.5(18800) | C$_{12}$H$_{17}$N$_3$O$_2$ | 61.26 (61.38) | 7.28 (7.15) | 17.86 (17.69) |

TABLE 1-continued

Structure: CH₃—N(R¹)—C(=O)—N(R²)—C(=O)—NH—R³

| Compound No. | R¹ | R² | R³ | Reaction process | MP, (°C.) | UV λ$_{max}^{cyclohexane}$ mμ (ε) | Molecular formula | C Calculated: (Found:) | H | N |
|---|---|---|---|---|---|---|---|---|---|---|
| 23 | —CH₃ | —CH₃ | 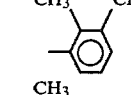 | B | 104–105 | 247(13100) | $C_{13}H_{19}N_3O_2$ | 62.63 (62.87) | 7.68 (7.96) | 16.85 (16.80) |
| 24 | —CH₃ | —CH₃ | 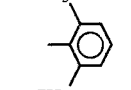 | B | 102–105 | 227(sh) | $C_{13}H_{19}N_3O_2$ | 62.63 (62.66) | 7.68 (7.75) | 16.85 (16.80) |
| 25 | —CH₃ | —CH₃ | 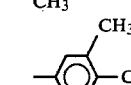 | B | 115–117 | 248(25400) | $C_{13}H_{19}N_3O_2$ | 62.63 (62.71) | 7.68 (8.00) | 16.85 (16.67) |
| 26 | —CH₃ | —CH₃ | 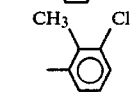 | B | 102–103 | 247.5(15400) | $C_{12}H_{16}ClN_3O_2$ | 53.44 (53.20) | 5.98 (6.06) | 15.58 (15.58) |
| 27 | —CH₃ | —CH₃ | 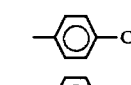 | B | 110–112 | 283(25800) | $C_{13}H_{17}N_3O_3$ | 59.30 (59.30) | 6.51 (6.65) | 15.96 (15.82) |
| 28 | —CH₃ | —CH₃ | 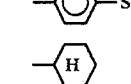 | B | 59–61 | 282(20700) | $C_{12}H_{17}N_3O_2S$ | 53.91 (53.72) | 6.41 (6.44) | 15.72 (15.90) |
| 29 | —CH₃ | —CH₃ | 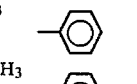 | B | 79–80 | Not available | $C_{11}H_{21}N_3O_2$ | 58.12 (57.95) | 9.31 (9.60) | 18.49 (18.15) |
| 30 | —CH₃ | —CH₂CH₃ | 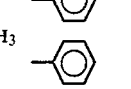 | B | 104.5–106.5 | 245(16800) | $C_{12}H_{17}N_3O_2$ | 61.26 (61.61) | 7.28 (7.55) | 17.86 (18.05) |
| 31 | —CH₃ | —(CH₂)₂CH₃ | 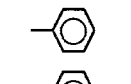 | B | 102–104.5 | 245(17600) | $C_{13}H_{19}N_3O_2 \cdot \frac{1}{4}H_2O$ | 61.52 (61.51) | 7.75 (7.94) | 16.56 (16.65) |
| 32 | —CH₃ | —(CH₂)₃CH₃ | 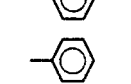 | B | 92–93.5 | 245(14100) | $C_{14}H_{21}N_3O_2$ | 63.86 (63.85) | 8.04 (8.47) | 15.96 (15.97) |
| 33 | —CH₂CH₃ | —CH₃ | 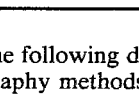 | A-2 | 88.5–90.5 | 244.5(13400) | $C_{12}H_{17}N_3O_2$ | 61.26 (61.25) | 7.28 (7.44) | 17.86 (17.61) |
| 34 | —(CH₂)₂CH₃ | —CH₃ | 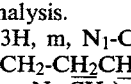 | A-2 | 63–64 | 244(19200) | $C_{13}H_{19}N_3O_2$ | 62.63 (62.84) | 7.68 (7.65) | 16.85 (16.88) |
| 35 | —(CH₂)₃CH₃ | —CH₃ | 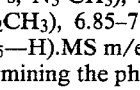 | A-2 | Oily product | | $C_{14}H_{21}N_3O_2$ | (a) | | |

In Table 1, (a) indicates the following data obtained by NMR and mass-spectrography methods in place of data obtained by elemental analysis.

(a) NMR(CDCl₃)δ: 0.94 (3H, m, N₁-CH₂CH₂CH₂-C$\underline{H}$₃), 1.07–1.80 (4H, m, N₁-CH₂-C$\underline{H}_2$C$\underline{H}_2$-CH₃), 2.90 (3H, s, N₁—CH₃), 3.12 (3H, s, N₃-CH₃), 3.24 (2H, q, J=8.0 Hz, N₁-C$\underline{H}_2$-CH₂CH₂CH₃), 6.85–7.51 (5H, m, Ar—H), 9.47 (1H, broad s, N₅—H).MS m/e: 263 (M⁺).

Next, several tests for determining the pharmacological properties, in that acute toxicity, anti-pyretic activity, analgesic activity and anti-inflammatory activity of the present 1,1,3,5-substituted biuret compounds of the formula (1) were conducted and the test results are shown in Table (2). In the tests, each compounds to be tested was used as a suspension in 0.25% carboxymethylcellulose solution. Methods for testing are explained as follows:

1. Acute toxicity

The ddy strain of male mice (body weight, 20–25 g) were used as test animals. The mice were fasted overnight and the compound to be tested was administered orally. General symptom of the mouse after the administration was observed for 7 days. The lethal dose (mg/kg, body weight) of the test compound was determined in connection with the death number of mice/the number of mice tested. In Table 2, the values indicated with Δ marks are 50% lethal dose, LD₅₀ (mg/kg, body weight).

2. Anti-pyretic activity

According to the method reported by Tanabe [*Folia Pharmacologia Japonica*, Vol. 73, pp. 803 (1977)], the Wistar strain of male rats (150–180 g body weight) were used as test animals. The rats were fasted overnight, and 1 ml/100 g (body weight) of 10% dry-yeast suspension were subcutaneously injected on the back of the rats. Five hours after the injection, the test compound was administered orally, then the body temperature of the rat was measured at time sequences. Anti-pyretic activity of the test compound was determined as the FI (febril index) by integrating pyrogenetic curve up to 4 hours after the administration of the test compound with time, and indicated as inhibitory ratio (%) shown by the following formula, $$\text{Inhibitory ratio (\%)} = \left(1 - \frac{\begin{pmatrix}\text{FI of the test group}\\ \text{of rats administered}\\ \text{with test compound}\end{pmatrix}}{\begin{pmatrix}\text{FI of control group}\\ \text{of rats}\end{pmatrix}}\right) \times 100$$

3 Analgesic activity (1) Acetic acid-induced stretching method

According to the method reported by Koster et al., [Fed. Proc., Vol. 18, pp. 412 (1959)], the ddy strain of male mice (body weight, 20-25 g) were used as test animals. The mice were fasted overnight, 100 mg/kg body weight of the test compound was administered orally, then 1 hour after the administration, 0.2 ml of 0.7% acetic acid solution was injected intraperitoneally. The acetic acid-induced stretching symptom of mouse was observed. Analgesic activity of the test compound was calculated as the inhibitory ratio (%). In Table 2, the values in Parentheses show the data obtained from the test by using the dosage other than 100 mg/kg body weight. Further, the values indicated with Δ marks show 50% effective dose, $ED_{50}$ (mg/kg body weight).

(2) Haffner method

According to the modified method reported by Fujimura et al., [*Bulletin of the Institute for Chemical Research*, Kyoto University, No. 25, pp. 36 (1951)], the ddy strain of male mice (body weight, 20-25 g) were used as test animals. The mice were fasted overnight, 100 mg/kg body weight of the test compound was administered orally, then 45 minutes after the administration, the threshold amount (1.5-2.5 mg/kg body weight) of morphine hydrochloride was injected subcutaneously. Then 1-hour pain reaction of the mouse caused by a clamp was observed. Analgesic activity of the test compound was calculated as the inhibitory ratio (%). In Table 2, the values in parentheses show the data obtained from the test by using the dosage other than 100 mg/kg body weight. Further, the values indicated with Δ marks show 50% effective dose, $ED_{50}$ (mg/kg body weight).

4. Anti-inflammatory activity

According to the method of acute carrageenin-induced inflammatory test [*Folia Pharmacologia Japonica*, Vol. 56, pp. 575 (1960)], the Wistar strain of male rats (body weight, 150-180 g) were used as test animals. The rats were fasted overnight, 100 mg/kg body weight of the test compound was administered orally, then 1 hour after the administration, 0.1 ml of 1% carrageenin solution, as the inflammation inducing agent, was injected subcutaneously to the hindpaw of the rat and the volume of the hindpaw was measured at time sequences. Anti-inflammatory activity of the test compound was calculated as inflammation inhibitory ratio (%) at 3 hours after the injection of the inflammation inducing agent.

TABLE 2

| Compound No. | Acute toxicity (mg/kg) | Anti-pyretic activity (%) | Analgesic activity | | Anti-inflammatory activity (%) |
|---|---|---|---|---|---|
| | | | Acetic acid-induced stretching method | Haffner method | |
| 1 | Δ1709 | 80 | Δ75(43-132) | Δ68(52-88) | 59 |
| 2 | 1000-¼ 2000-4/4 | 76 | 62.5 | 75 | 63 |
| 3 | Δ930 | 61 | 87.5 | 62.5 | 37 |
| 4 | 500-0/4 1000-4/4 | 33 | 87.5 | 50 | 24 |
| 5 | 2000-0/4 | 66 | 50 | 37.5 | 38 |
| 6 | Δ1481 | 43 | 62.5 | 75 (200 mg/kg) | 30 (2 hours value) |
| 7 | Δ1200 | 84 | Δ12(4-36) | Δ20(11-35) | 47 |
| 8 | 1000-0/4 2000-¾ | 42 | 50 | 75 | |
| 9 | Δ1100 | 29 | 50 | 50 | 25 |
| 10 | 1000-¼ 2000-¾ | 43 | 50 | 62.5 | |
| 11 | Δ1353 | 103 | Δ60(48-76) | Δ74(49-113) | 48 (2 hours value) |
| 12 | 1000-¼ | 65 | 12.5 | 37.5 | 66 |
| 13 | 1000-0/4 2000-4/4 | 62 | 37.5 | Δ64(37-112) | 32 (2 hours value) |
| 14 | 2000-0/4 | 26 | 62.5 | 50 | 32 (2 hours value) |
| 15 | 500-2/4 | 26 | 100 | 50 | 32 |
| 16 | 1000-0/4 2000-2/4 | 13 | 37.5 | 25 | 35 (2 hours value) |
| 17 | Δ1800 | 75 | Δ39(21-73) | Δ(42-153) | 33 |
| 18 | 1000-0/4 2000-4/4 | 18 | 75 | 62.5 | |
| 19 | 500-0/4 1000-2/4 | 23 | Δ38(18-80) | 62.5 | 30 |
| 20 | Δ1000 | 41 | 37.5 | 50 | 29 |
| 21 | 2000-2/4 | 31 | 75 | 37.5 | 28 |
| 22 | 2000-0/4 | 52 | Δ33(14-78) | Δ80(42-152) | 23 (2 hours value) |
| 23 | 1000-¼ 2000-4/4 | 40 | 50 | 25 | |
| 24 | Δ595 | 69 | 75 | 37.5 | |
| 25 | 2000-¼ | 31 | 87.5 (60 mg/kg) | Δ86(57-129) | |
| 26 | 1000-¼ | 45 | 75 | 25 | |

TABLE 2-continued

| Compound No. | Acute toxicity (mg/kg) | Anti-pyretic activity (%) | Analgesic activity | | Anti-inflammatory activity (%) |
|---|---|---|---|---|---|
| | | | Acetic acid-induced stretching method | Haffner method | |
| 27 | 2000–4/4 500–0/4 | 36 | 62.5 | 37.5 | 31 (2 hours value) |
| 28 | 1000–4/4 1000–0/4 | | 50 | | |
| 29 | 2000–4/4 Δ1447 | | 87.5 (200 mg/kg) | 25 | 24 (2 hours value) |
| 30 | 1000–0/4 2000–¾ | 12 | 62.5 | | 23 |
| 31 | 2000–0/4 | 12 | 37.5 | 62.5 (200 mg/kg) | |
| 32 | 1000–0/4 2000–¾ | 18 | 37.5 | 31 | |
| 33 | Δ1288 | 49 | 50 (80 mg/kg) | Δ100(50–170) | 34 |
| 34 | 1000–¼ 2000–4/4 | 44 | 75 (60 mg/kg) | 37.5 | 26 (2 hours value) |
| 35 | 1000–0/4 2000/14 ¾ | 35 | 37.5 | 25 | |

The followings are examples of preparations for analgesic, anti-pyretic or anti-inflammatory composition containing 1,1,3,5-substituted biuret compound as the active ingredient.

Preparation 1

| Ingredients | Amount (mg) |
|---|---|
| 1,1,3-Trimethyl-5-phenylbiuret (Compound No. 1) | 200 |
| Lactose | 500 |
| Corn starch | 280 |
| Hydroxypropylcellulose | 20 |
| To make one package contains | 1,000 |

By using the ingredients in the above-mentioned formulation, a granular preparation was prepared by conventional methods.

Preparation 2

| Ingredients | Amount (mg) |
|---|---|
| 1,1,3-Trimethyl-5-(4-chlorophenyl)biuret (Compound No. 7) | 100 |
| Lactose | 85 |
| Crystalline cellulose | 50 |
| Hydroxypropylstarch | 30 |
| Talc | 4 |
| Magnesium stearate | 1 |
| To make one tablet contains | 270 |

By using the ingredients in the above-mentioned formulation, tablets were prepared by conventional methods.

Preparation 3

| Ingredients | Amount (mg) |
|---|---|
| 1,1,3-Trimethyl-5-(4-bromophenyl)biuret (Compound No. 11) | 100 |
| Lactose | 50 |
| Potate starch | 50 |
| Crystalline cellulose | 109 |
| Magnesium stearate | 1 |
| To make one capsule contains | 310 |

By using the ingredients in the above-mentioned formulation, a capsule preparation was prepared by conventional methods.

Preparation 4

| Ingredients | Amounts (mg) |
|---|---|
| 1,1,3-Trimethyl-5-(2,3,5,6-tetrafluorophenyl)biuret (Compound No. 22) | 200 |
| Lactose | 100 |
| Crystalline cellulose | 98 |
| Magnesium stearate | 2 |
| To make one capsule contains | 400 |

By using the ingredients in the above-mentioned formulation, a capsule preparation was prepared by conventional methods.

Preparation 5

| Ingredients | Amounts (mg) |
|---|---|
| 1,1,3-Trimethyl-5-(3,4,5-trimethoxyphenyl)biuret (Compound No. 19) | 250 |
| Witepzol W-35 (A trade name for a suppository base material manufactured by and sold from Dynamite Nobel Company.) | 750 |
| To make one suppository contains | 1,000 |

By using the ingredients in the above-mentioned formulation, a suppository preparation was prepared by conventional methods.

Preparation 6

| Ingredients | Amounts (mg) |
|---|---|
| 1,1,3-Trimethyl-5-(4-methoxyphenyl)biuret (Compound No. 17) | 100 |
| Sodium chloride | 16 |
| Distilled water for injection | q.s. |
| To make one ampule contains | 2 ml |

By using the ingredients in the above-mentioned formulation, an injection preparation (ampule) was prepared by conventional methods.

Preparation 7

| Ingredient | Amount (g) |
| --- | --- |
| 1,1,3-Trimethyl-5-(3,4-dimethyl-phenyl)biuret (Compound No. 25) | 2.0 |
| White vaseline | 23.0 |
| Stearyl alcohol | 22.0 |
| Propylene glycol | 12.0 |
| Sodium laurylsulfate | 1.5 |
| Ethyl p-oxybenzoate | 0.025 |
| Propyl p-oxybenzoate | 0.015 |
| Purified water | q.s. |
| To make the whole | 100 |

By using the ingredients in the above-mentioned formulation, an ointment preparation was prepared by conventional methods.

What is claimed is:

1. A 1,1,3-trimethyl-5-substituted biuret compound of the formula:

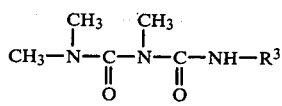

wherein

R³ is a cyclohexyl group or a phenyl group which may be unsubstituted or may have at least one substituent selected from the group consisting of chlorine, bromine, fluorine, methyl, trifluoromethyl, dimethylamino, methoxy, methylthio, nitro and acetyl.

2. Compound of claim 1, wherein R³ is substituted or unsubstituted phenyl.

3. 1,1,3-Trimethyl-5-phenylbiuret as claimed in claim 1.

4. 1,1,3-Trimethyl-5-(2-fluorophenyl)biuret as claimed in claim 1.

5. 1,1,3-Trimethyl-5-(4-fluorophenyl)biuret as claimed in claim 1.

6. 1,1,3-Trimethyl-5-(2,3,5,6-tetrafluorophenyl)biuret as claimed in claim 1.

7. 1,1,3-Trimethyl-5-(2-chlorophenyl)biuret as claimed in claim 1.

8. 1,1,3-Trimethyl-5-(3-chlorophenyl)biuret as claimed in claim 1.

9. 1,1,3-Trimethyl-5-(4-chlorophenyl)biuret as claimed in claim 1.

10. 1,1,3-Trimethyl-5-(2,4-dichlorophenyl)biuret as claimed in claim 1.

11. 1,1,3-Trimethyl-5-(2,6-dichlorophenyl)biuret as claimed in claim 1.

12. 1,1,3-Trimethyl-5-(3,4-dichlorophenyl)biuret as claimed in claim 1.

13. 1,1,3-Trimethyl-5-(4-bromophenyl)biuret as claimed in claim 1.

14. 1,1,3-Trimethyl-5-(2-trifluoromethylphenyl)-biuret as claimed in claim 1.

15. 1,1,3-Trimethyl-5-(3-trifluoromethylphenyl)-biuret as claimed in claim 1.

16. 1,1,3-Trimethyl-5-(4-dimethylaminophenyl)-biuret as claimed in claim 1.

17. 1,1,3-Trimethyl-5-(4-nitrophenyl)biuret as claimed in claim 1.

18. 1,1,3-Trimethyl-5-(2-methyoxyphenyl)biuret as claimed in claim 1.

19. 1,1,3-Trimethyl-5-(4-methoxyphenyl)biuret as claimed in claim 1.

20. 1,1,3-Trimethyl-5-(3,4-dimethoxyphenyl)biuret as claimed in claim 1.

21. 1,1,3-Trimethyl-5-(3,4,5-trimethoxyphenyl)biuret as claimed in claim 1.

22. 1,1,3-Trimethyl-5-(2-methylphenyl)biuret as claimed in claim 1.

23. 1,1,3-Trimethyl-5-(3-methylphenyl)biuret as claimed in claim 1.

24. 1,1,3-Trimethyl-5-(4-methylphenyl)biuret as claimed in claim 1.

25. 1,1,3-Trimethyl-5-(2,3-dimethylphenyl)biuret as claimed in claim 1.

26. 1,1,3-Trimethyl-5-(2,6-dimethylphenyl)biuret as claimed in claim 1.

27. 1,1,3-Trimethyl-5-(3,4-dimethylphenyl)biuret as claimed in claim 1.

28. 1,1,3-Trimethyl-5-(2-methyl-3-chlorophenyl)-biuret as claimed in claim 1.

29. 1,1,3-Trimethyl-5-(4-acetylphenyl)biuret as claimed in claim 1.

30. 1,1,3-Trimethyl-5-(4-methylthiophenyl)biuret as claimed in claim 1.

31. 1,1,3-Trimethyl-5-cyclohexylbiuret as claimed in claim 1.

32. A process for preparing the substituted biuret compound of claim 1, said process comprising reacting an allophanoyl chloride of formula (4).

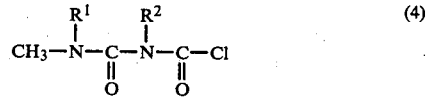

wherein R¹ and R² are defined in claim 1, with an amine of formula (5)

wherein R³ is defined in claim 1, at a temperature of about −20° C. to about 50° C. to produce said 1,1,3,5-substituted biuret compound.

33. A process for preparing the 1,1,3,5-substituted biuret compound of claim 1, said process comprising reacting an allophanoyl chloride of formula (6)

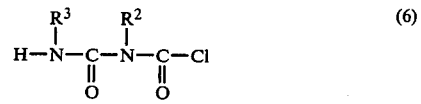

wherein R² and R³ are defined in claim 1, with an amine of formula (7)

wherein R¹ is defined in claim 1, at a temperature of about −20° C. to about 50° C. to produce said 1,1,3,5-substituted biuret compound.

* * * * *